Figure 1:
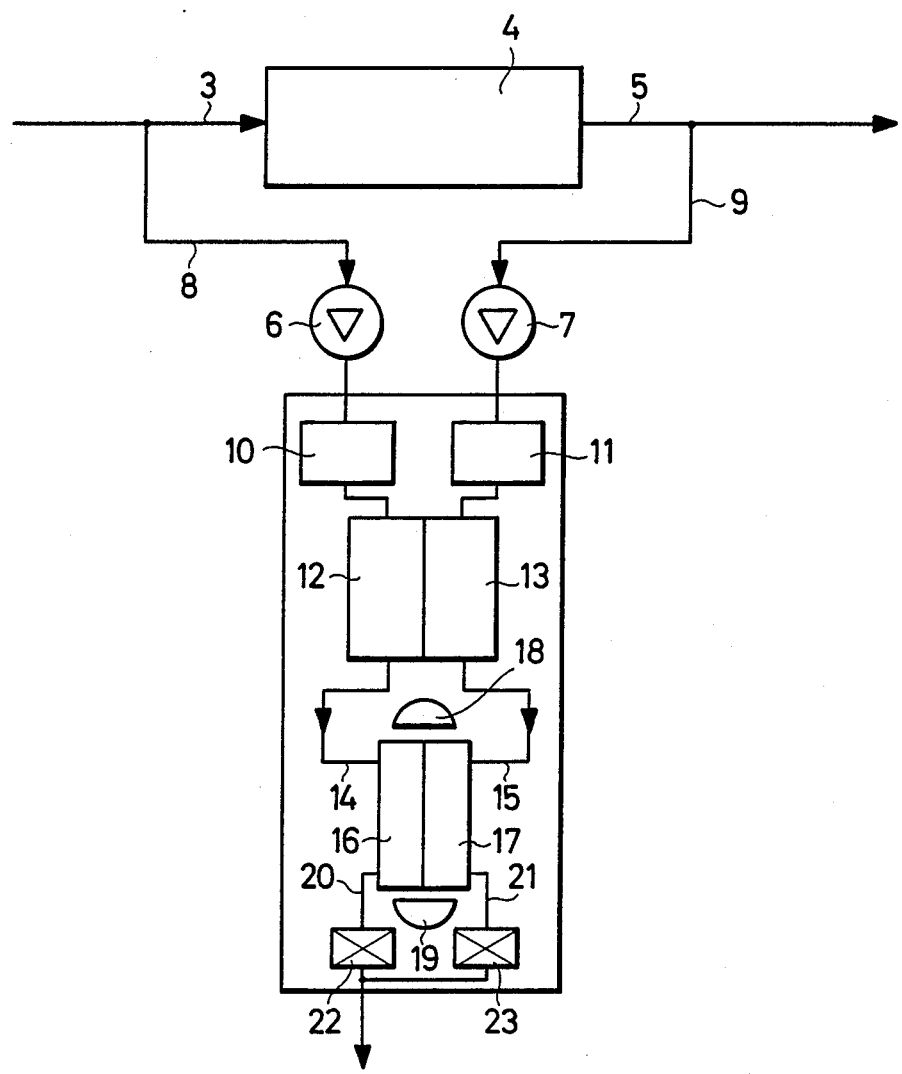

United States Patent [19]

Mayer

[11] Patent Number: 4,931,660

[45] Date of Patent: Jun. 5, 1990

[54] APPARATUS FOR MEASURING FOREIGN SUBSTANCE CONTENT IN FLOWING LIQUIDS

[75] Inventor: Juergen Mayer, Hanau, Fed. Rep. of Germany

[73] Assignee: Leybold Aktiengesellschaft, Cologne, Fed. Rep. of Germany

[21] Appl. No.: 127,072

[22] Filed: Dec. 1, 1987

[30] Foreign Application Priority Data

Oct. 3, 1987 [DE] Fed. Rep. of Germany ....... 3733573

[51] Int. Cl.⁵ ............................................. G01N 15/06
[52] U.S. Cl. ..................................... 250/575; 356/440
[58] Field of Search ............... 250/573, 574, 575, 576, 250/373; 356/434, 435, 440

[56] References Cited

U.S. PATENT DOCUMENTS

| 3,535,044 | 10/1970 | Seward | 356/409 |
| 3,588,496 | 6/1971 | Snowman | 356/434 |
| 4,176,963 | 12/1979 | Fabinski et al. | 356/435 |
| 4,591,721 | 5/1986 | Wong | 250/373 |

FOREIGN PATENT DOCUMENTS

| 2147142 | 10/1974 | Fed. Rep. of Germany . |
| 2720636 | 11/1978 | Fed. Rep. of Germany . |
| 3023625 | 6/1979 | Fed. Rep. of Germany . |
| 2949438 | 6/1980 | Fed. Rep. of Germany . |
| 3112308 | 10/1982 | Fed. Rep. of Germany . |
| 2818841 | 6/1984 | Fed. Rep. of Germany . |
| 2328328 | 8/1985 | Fed. Rep. of Germany . |
| 979850 | 1/1965 | United Kingdom . |

*Primary Examiner*—David C. Nelms
*Assistant Examiner*—Eric F. Chatman
*Attorney, Agent, or Firm*—Felfe & Lynch

[57] ABSTRACT

In an apparatus for determining the concentration of foreign substances in a stream of water, a liquid stream is derived from lines preceding and following the pipeline block for the process and each is pumped into a cell, a radiation source being associated with each of the cells, whose beams penetrate the cells and are delivered both to a first detector and to a second detector. A beam filter is placed in front of each of the detectors and divides the beams into two beams of different wavelengths. Between the beam source and the two cells a revolving chopper wheel is disposed which alternately deflects the beams of the radiation source into one and the other cell, while the electrical signals of the detectors are compared with one another by an electrical circuit and processed to an identifying signal.

7 Claims, 3 Drawing Sheets

APPARATUS FOR MEASURING FOREIGN SUBSTANCE CONTENT IN FLOWING LIQUIDS

The invention relates to an apparatus for measuring the foreign substance content in flowing liquids, especially for determining the concentration of aromatic hydrocarbons in a stream of water.

Apparatus for measuring the foreign substance concentration in a gas stream are known, which serve for process control in chemical apparatus, for measuring flue gas, and for measuring emissions from furnaces and from motor vehicles. This known apparatus operates by the nondispersive ultraviolet absorption method of measurement. The specific radiation absorption in the ultraviolet range by the component being measured serves as the measuring effect.

The ultraviolet radiation is produced in a hollow-cathode lamp. A shutter wheel divides the radiation into two beams separate in time and a beam splitter divides it into two beams separate in space. The measuring beam strikes a receiver and is carried through the measuring cell. The completely unaffected control beam strikes the correction receiver.

The electronic processing of these 4 signals eliminates the influence of nonselective absorptions, such as for example cell contamination, and aging effects in radiator and receiver.

The present invention is addressed to the task of creating an apparatus which in flow-through operation performs a comparative measurement between the control and sample and which is adapted to operate a limit switch upon the exceeding of a predetermined concentration of the foreign substance.

This task is accomplished according to the invention in that both before and after the pipeline block for the process a liquid stream is derived through conduits and each is delivered to a cell, a radiation source being associated with each of the two cells whose beams pass through the cells and are fed each both to a first detector and to a second detector, a beam filter being placed in front of each of the detectors which divides the beams into two beams of different wavelength, and between the beam source and the two cells a rotating chopper wheel is disposed which alternately deflects the beams of the radiation source into the one and the other cell, the electrical signals of the detectors being compared by an electrical circuit and processed to form an identifying signal.

Additional features, details and embodiments of the invention will be found in the appended claims.

The advantage achieved by the invention is to be seen essentially in the fact that, in a large technical apparatus, a continuous monitoring of the output water or waste water can be performed for a long period of time during an ongoing process, while the percentage of contamination of the input water is detected and distinguished from the percentage of contamination produced by the process.

Figure 2:
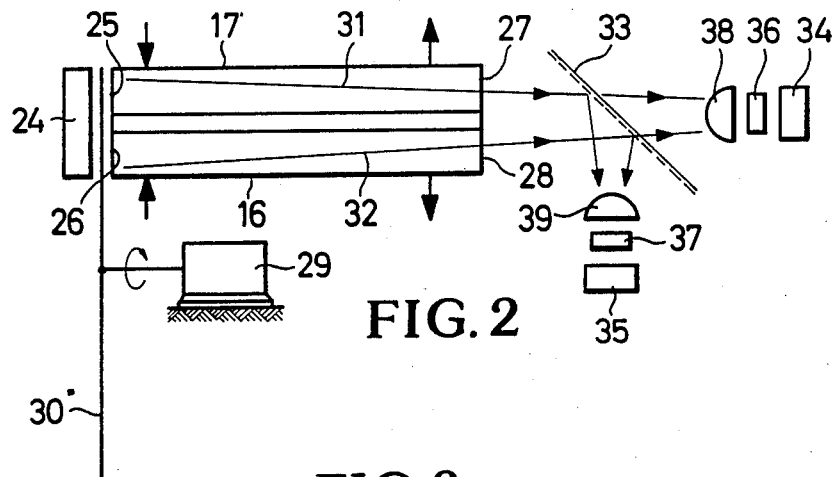
Figure 3:
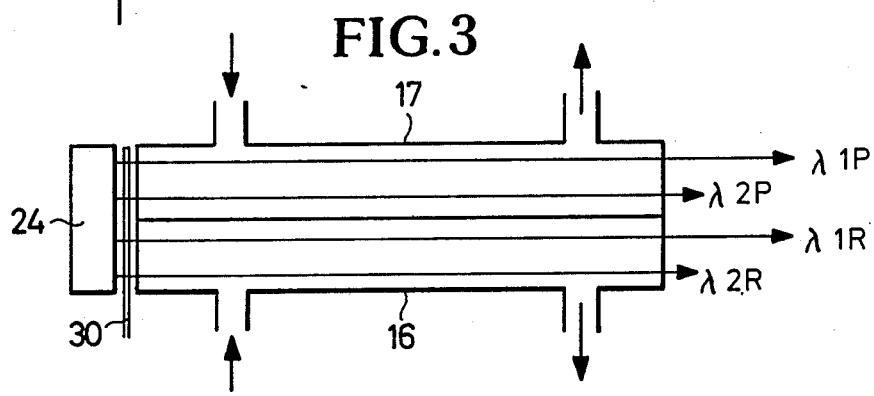
Figure 4:
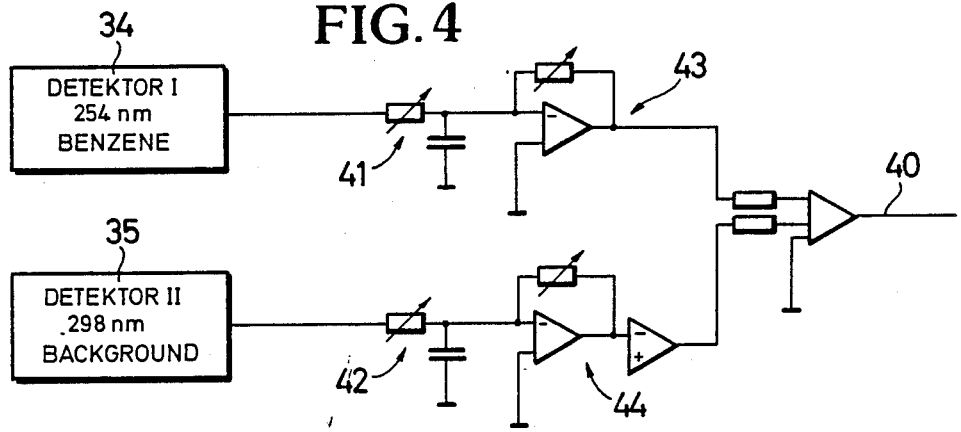
Figure 5:
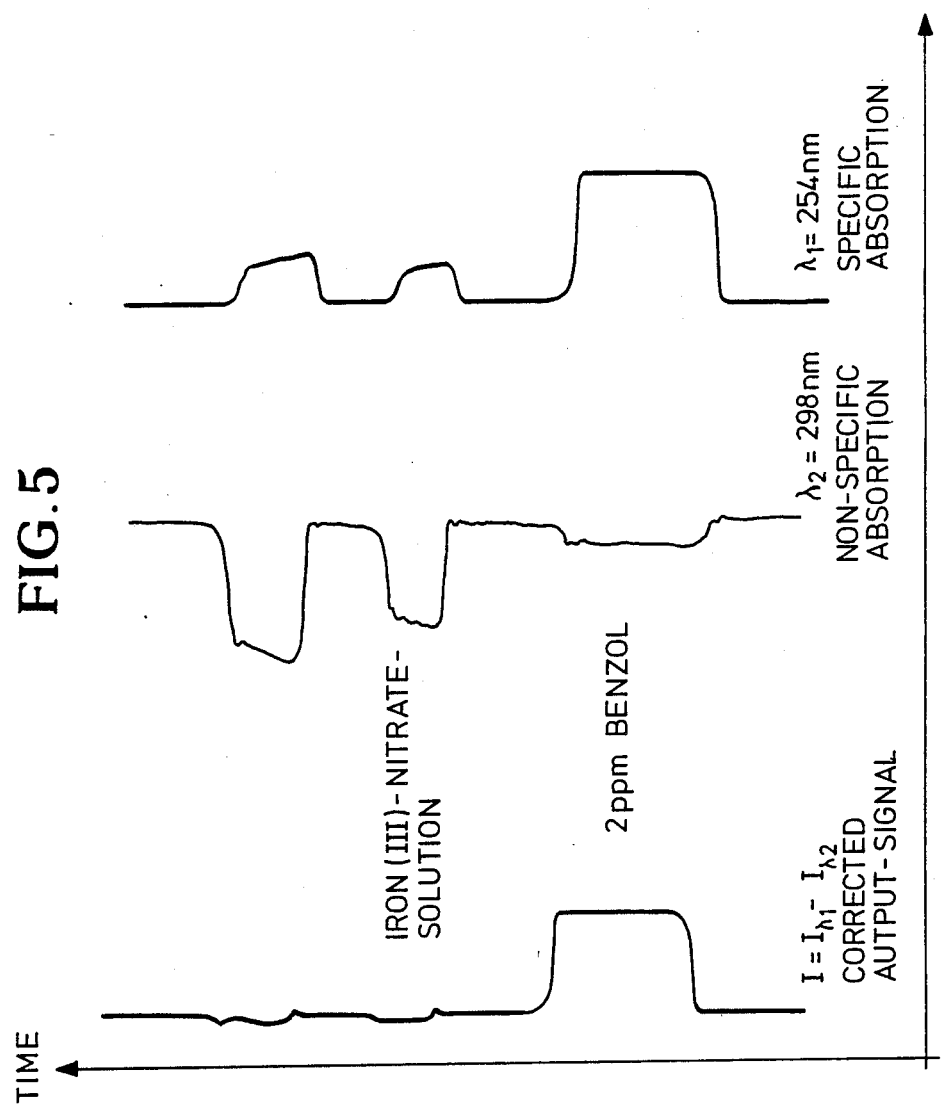

The invention admits of a great variety of embodiments; one of them is represented diagrammatically in the appended drawings, wherein FIG. 1 is a circuit diagram of an apparatus for the ongoing determination of the benzene content of running water, FIG. 2 shows the construction of the measuring system of the apparatus according to FIG. 1, FIG. 3 shows the cell of the measuring system according to FIG. 1, FIG. 4 is a representation of the electrical circuit connected to the detectors of the measuring apparatus, FIG. 5 shows three measuring curves written by a recording meter for benzene in water.

Figure 6:
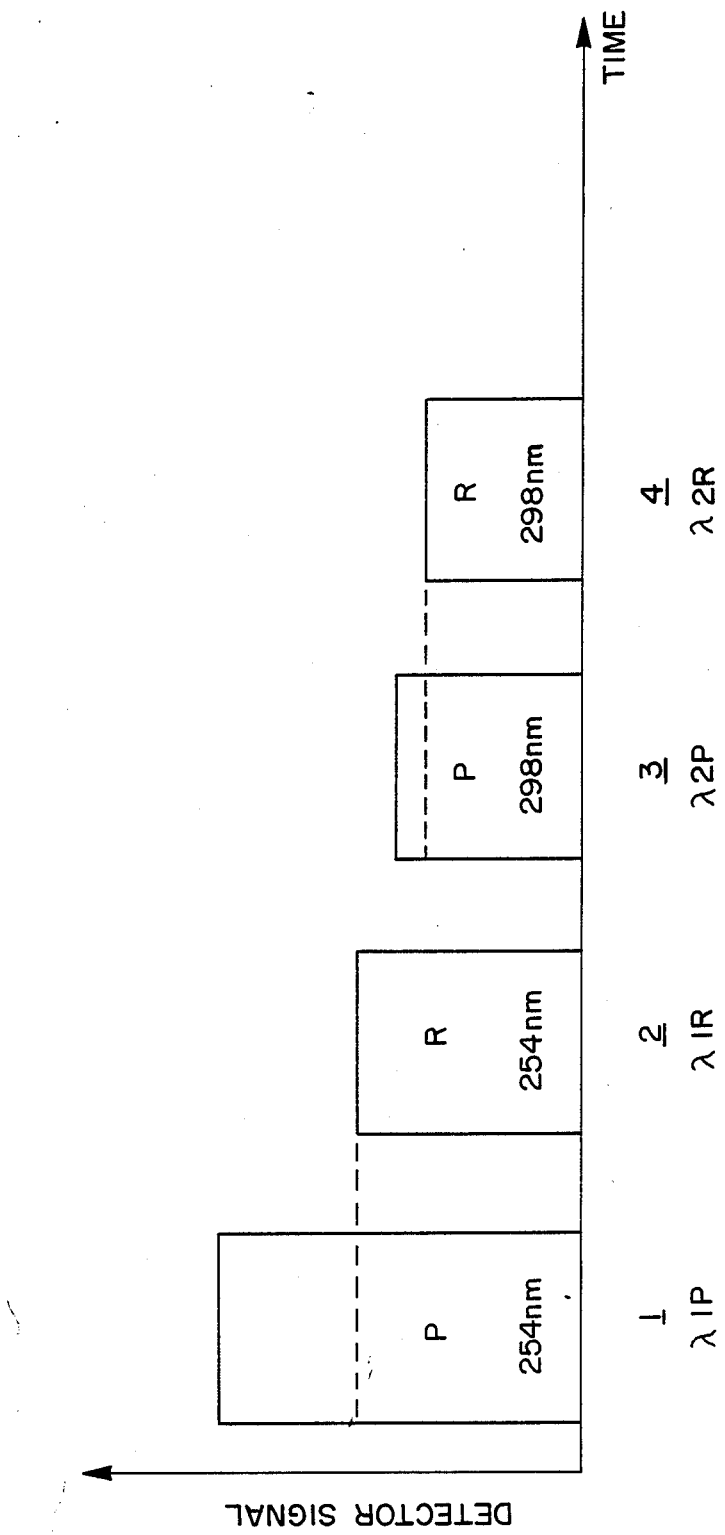

FIG. 6 is a graph showing the detector signal vs. time.

The apparatus according to FIG. 1 consists essentially of a pipe line 3 carrying comparatively clean input water, a block of piping 4 required for a process, a pipeline 5 carrying the output water possibly contaminated by the process, the two bypass lines 8 and 9 and the pumps 6 and 7 inserted therein, the two bubble separators 10 and 11, the heat exchangers 12 and 13 connected to the output of the bubble separators 10 and 11, the branch lines 14 and 15 which are connected to the cells 16 and 17, the light source 18 and the detector 19, the two drain lines 20 and 21, and lastly the magnetic valves 22 and 23 are inserted into the drain lines.

The apparatus operates as follows: A stream of water from the input water flowing to the piping block 4 is tapped from pipeline 3 through the branch line 8 by the pump 6 and is then pumped into the bubble separator 10 and from there to the heat exchanger 12. The temperature-controlled water stream rendered largely bubble-free by the two units 6 and 12 is then pumped through the cell 16 and then into the drain line 20. At the same time a second stream of water is tapped from the output water through the branch line 9 and heat exchanger 13 into the second cell 17 and then into the drain line 21.

As it can be seen in FIG. 2, an ultraviolet light source 24 is associated with the two cells 16 and 17, and its beams pass through the cells 16 and 17 and the water present in the latter, since the front and rear end walls 25–26 and 27–28 of the cells are made of transparent material.

Between the cells 16 and 17 and the ultraviolet light source a perforated disk 30 driven by a motor 29 rotates such that the beams 31 and 32 fall alternately on a semitransparent mirror 33 which reflects them to the detectors 34 and 35 (represented in FIG. 1 by a symbol 19). A light filter 36 and 37 for 254 nm and 298 nm respectively, for example, is situated in front of the detectors 34 and 35, respectively. Furthermore, condenser lenses 38 and 39 are provided which steer the beams 31 and 32 to the detectors 34 and 35, respectively. The electrical signals produced by the two detectors 34 and 35 are processed in the electrical circuit shown in FIG. 4 to produce a signal which is present at the electrical conductor 40. The circuit itself has an RC filter 41 and 42 and amplifier circuits 43 and 44 which process the electrical signals delivered by the detectors 34 and 35.

While the two streams of water are being pumped uniformly by the pumps 6 and 7 through the cells 16 and 17, the chopper wheel rotates at uniform speed so that for each rotation of the chopper four readings can be obtained in parallel:

| | |
|---|---|
| Specific absorption on the reference side: | $\lambda 1R$ [2] |
| Nonspecific absorption on the reference side: | $\lambda 2R$ [4] |
| Specific absorption on the sample side: | $\lambda 1P$ [1] |
| Nonspecific absorption on the sample side: | $\lambda 1P$ [3] |

The chopper 30 alternately opens the beam path between the sample side 17 and the reference side 16, while the signals for the specific absorption λ1 and the nonspecific absorption λ2 are determined synchronously by two detectors 34 and 35.

This example shows that a nonspecific absorption (not by benzene?) takes place in reference [4].

With no specific absorptions, [3] and [4] would have to be equally large.

From this it must be concluded that [2] is also undervalued by the factor [3]/[4].

$$[2'] = [2] \cdot [3]/[4]$$

The actual signal therefore is the measurement obtained under [1] minus the corrected reference value [2'].

The corrected signal is thus computed as follows:

FIG. 6 is a graph showing the detector signal vs. time.

$$\text{Signal} = [1] - [2] \cdot [3]/[4]$$

i.e. from the detector signal which is generated on the sample side by specific absorption there is subtracted the signal which is generated on the reference side at 254 nm, respectively, while the signal on the reference side has been multiplied before at 298 nm, respectively, by the quotient from the signal on the sample side divided by the signal on the reference side.

I claim:

1. Apparatus for measuring the foreign substance content in flowing liquids, especially for determining the concentration of aromatic hydrocarbons in a water stream, comprising:
   a pipeline block for a process;
   conduits in front of and behind the pipeline block;
   a plurality of cells;
   first and second detectors;
   means for shunting a liquid current through said conduits in front of and behind said pipeline block for the process and for pumping flowing liquid currents into and through said cells;
   a radiation source associated with said cells and having beams which penetrate said cells and carry each beam to said first detector and to said second detector;
   beam filter means desposed in front of each of said detectors and dividing the beams into two beams of different wavelengths;
   a rotating chopper wheel disposed between said radiation source and two of said cells, which alternately steers the beams of said radiation source into the one cell and into the other cell; and
   electrical circuit means for comparing electrical signals of the detectors with one another and for processing said electrical signals to an identifying signal.

2. Apparatus according to claim 1, which includes a beam splitter comprising said beam filter means.

3. Apparatus according to claim 1, in which said two cells have the same dimensions and have end walls formed of transparent material.

4. Apparatus according to claim 1, which includes heat exchangers placed in front of said two cells which equalize the temperatures of two liquid currents pumped through said conduits.

5. Apparatus according to claim 1, which includes two drain lines behind said two cells and which includes valves, inserted into said two drain lines b-hind said two cells, which alternately open and close in rapid succession, so that pulsating liquid streams are produced in said drain lines.

6. Apparatus according to claim 2, in which said beam splitter divides said beams of said radiation source in a ratio of 50:50 and in which said beam filter means includes a filter disposed ahead of said first detector and transparent for a first relevant wavelength range and a filter disposed ahead of said second detector and transparent for a second relevant wavelength range.

7. Apparatus according to claim 1, in which said two cells each have a free cross-sectional area that is larger than the cross-sectional area of the associated beam in each case.

* * * * *

UNITED STATES PATENT AND TRADEMARK OFFICE
CERTIFICATE OF CORRECTION

PATENT NO. : 4,931,660

DATED : June 5, 1990

INVENTOR(S) : Juergen Mayer

It is certified that error appears in the above-identified patent and that said Letters Patent is hereby corrected as shown below:

Column 3, line 7 for "benzene?" read -- benzene! --.

Column 4, line 27 for "b-hind" read -- behind --.

Signed and Sealed this

Second Day of June, 1992

Attest:

DOUGLAS B. COMER

*Attesting Officer*     Acting Commissioner of Patents and Trademarks